United States Patent [19]

Carle

[11] 4,386,071
[45] * May 31, 1983

[54] INSECTICIDAL NATURAL BAIT COMPOSITION AND METHOD OF USING SAME

[76] Inventor: Arthur Carle, 3390 rue Simard, St-Hubert, Quebec, Canada, J3Y 6T4

[*] Notice: The portion of the term of this patent subsequent to Jul. 21, 1998, has been disclaimed.

[21] Appl. No.: 282,381

[22] Filed: Jul. 13, 1981

Related U.S. Application Data

[63] Continuation-in-part of Ser. No. 57,436, Jul. 13, 1979, Pat. No. 4,279,895.

[51] Int. Cl.³ .............................................. A01N 59/00
[52] U.S. Cl. ..................................................... 424/127
[58] Field of Search ............................ 426/1; 424/127

[56] References Cited

U.S. PATENT DOCUMENTS

| | | | |
|---|---|---|---|
| 4,049,460 | 9/1977 | Broadhent | 426/1 |
| 4,075,783 | 2/1978 | Burden et al. | 426/1 |
| 4,279,895 | 7/1981 | Carle | 424/127 |

OTHER PUBLICATIONS

Chem. Abstracts 88:P33200k.
Chem. Abstracts 93:127146c.
Chem. Abstracts 93:127157g.

Primary Examiner—Ethel G. Love

[57] ABSTRACT

Disclosed is an insecticidal composition based on diatomaceous silica and a sugar or sugar substitute and a method of using it.

14 Claims, No Drawings

INSECTICIDAL NATURAL BAIT COMPOSITION AND METHOD OF USING SAME

This application is a continuation-in-part of Ser. No. 057,436 filed July 13, 1979, now U.S. Pat. No. 4,279,895.

This invention relates to an insecticidal natural bait composition. More particularly, this invention relates to a composition which can be used as a bait for insects and which, by its nature, is capable of killing insects without polluting the environment. Even more specifically, the invention relates to a method of killing insects using the insecticidal natural bait composition according to this invention.

Presently, there are a large number of insecticidal compositions. Most of them are based on chemicals which are either capable of instantaneously killing insects or can provoke paralysis. With the knowledge which has been acquired on the effects of the insecticidal chemicals, there is presently a tendency to search for ways to get rid of insects without endangering the environment.

One way of doing it is to use a diatomaceous silica also called diatomite which, because of its very small particle size has very sharp edges. Such a composition has been defined in U.S. Pat. No. 3,159,536.

Presently, there is a popular insecticide which is called PERMAGUARD. This composition is made of pyrethrin and a diatomaceous earth. There is just enough pyrethrin in the composition to cause a partial paralysis in the insect, with the result that it is forced to crawl into the diatomaceous earth where it becomes injured and it rapidly dies. However, pyrethrin is a polluting agent and furthermore, after eight hours, its effect is completely gone by with the result that the insect does not have a tendency to be in contact with diatomaceous earth.

There is therefore a need to provide an insecticidal composition which is as much as possible free of polluting chemicals and which, at the same time, is effective in getting rid of insects.

I have found that it is possible to kill insects by using an insecticidal natural bait composition based on diatomaecous silica and a sugar.

In accordance with a broad embodiment of the invention, there is provided an insecticidal natural bait composition comprising
  (a) between about 75 and about 95% by weight of humidified diatomaceous silica having a particle size of at most 50 microns;
  (b) between about 5 and about 25 percent by weight of a sugar or a sugar substitute;
  (c) said composition being humidified to contain about 1 to about 25 percent by weight water to enable it to be swallowed by an insect, and to prevent said sugar or sugar substitute from being washed away from said composition.

In order to be effective, it has been found that the composition according to the invention must have a certain percentage of humidity. Preferably, the composition contains about 1 to about 25 percent by weight of water. A preferred composition contains about 5 to about 25 percent by weight of water. Generally, I use a composition containing 5 to about 12 percent by weight of water. A most preferred composition is one in which there is used a diatomaceous earth containing about 5.2 percent by weight of water.

A preferred diatomaceous silica which can be used in formulating the composition according to the invention is one in which the particle size varies up to at most 50 microns.

Although any diatomaceous silica having the above particle size can be used with success in treating insects, I prefer to use substances made by Johns-Manville and known under the trade marks CELITE 209 and CELITE 322.

Although any kind of sugar can be used, as long as an insect will be attracted by the insecticidal natural bait composition according to the invention, I prefer to use invert sugar such as LUMOLININE.

In order to destroy all kinds of insects, it is merely necessary to contact them with a spray of the composition according to the invention.

The invention will now be illustrated by means of the following examples.

EXAMPLE 1

A forest infested with gypsy moths was treated with the following composition:
  (1) CELITE 322 Filler (diatomaceous silica) 90 percent by weight;
  (2) LUMOLININE (invert sugar) 10 percent by weight.

The two ingredients were mixed thoroughly in a blender by controlling the humidity to at most 5 percent by weight. The powder composition was sprayed on each tree with a rotoduster during the night when the humidity is higher.

Results:
Fast knock-down after two hours of all caterpillars.

EXAMPLE 2

The same mixture was used in a grain elevator, however controlling the humidity to 10-12 percent by weight.

Examination of the grain revealed complete absence of living insects.

EXAMPLE 3

The same composition was used in a home infested with cockroaches, ants, fleas, wood termites and carpet termites. After spraying the entire home with the composition according to the invention, it was realized that two hours after the treatment, all the insects were dead.

EXAMPLE 4

A small garden was treated with the same composition and it was found that it was successful to kill ants, worms, etc.

It would seem that the way the composition acts on the insects, is that the insect is attracted to it by the sugar or sugar substitute which is impregnated in the pores of the diatomaceous silica. The insects thereafter swallow the composition because it is naturally attracted to sugar. Tests made on cockroaches which had died after eating the composition according to the invention reveal that their bowels are all perforated. It would seem that the damage caused to the bowels of the insects results in rapid death followed by desiccation.

EXAMPLE 5

For the tests we used the following items:
Sitophilus oryzae as test insects
Wheat as grain
Copper rings 5.1 cm. in diameter and 2 cm. high Filter papers and petri dishes
One glass jar, 32 oz.
We coated the inside surfaces of the copper rings to prevent insects from climbing the sides
We made four different tests
1. We powdered a filter paper with the natural product (diatomaceous earth and invert sugar). We placed a copper ring on the filter and 20 Sitophilus oryzae in the center.
2. We placed 20 S. oryzae on a filter paper inside a ring and we powdered the insects with the natural product.
3. On a filter paper and inside a ring we placed a small pile of the natural product and on the other side we placed few pieces of wheat and 20 S. oryzae.
4. We prepared a mixture as follows: 1 oz. of natural product with 18 pounds of grain. Then we mixed 8 oz. of this mixture with 20 S. oryzae in a glass jar.

After 24 hours
Half of the insects in each case were knocked down (KD). Insects classified as KD are on their backs or sides and are unable to walk.

After 48 hours
All insects in each case were knocked down.
These tests were done three times the same way and each time we had the same results.

EXAMPLE 6

The composition contains 10% sucrose and 90% diatomaceous earth. Humidity controlled to at most 5 percent by weight. Effective against onion flies, ants, cockroaches and caterpillars.

EXAMPLE 7

Same results obtained used the following sugars:
(a) 8% inverted sugar + 2% honey;
(b) 10% glucose;
(c) 8% glucose + 2% honey;
(d) 10% icing sugar;
(e) 10% sucrose;
(f) 8% sucrose + 2% honey;
(g) 10% dextrose;
(h) 8% dextrose + 2% honey.

I claim:

1. An insecticidal natural bait comprising
   (a) between about 75 and about 95 percent by weight of humidified diatomaceous silica having a particle size of at most 50 microns;
   (b) between about 5 and about 25 percent by weight of sugar or a sugar substitute;
   (c) said composition being humidified to contain about 1 to about 25 percent by weight water to enable it to be swallowed by an insect and to prevent said sugar or sugar substitute from being washed away from said composition.

2. An insecticidal natural bait composition according to claim 1 wherein said composition contains about 5 to about 25 percent by weight of water.

3. An insecticidal natural bait composition according to claim 1 wherein said composition contains about 5 to about 12 percent by weight of water.

4. An insecticidal natural bait composition according to claim 1 wherein said composition contains about 5.2 percent by weight of water.

5. An insecticidal natural bait composition according to claim 1 wherein said diatomaceous silica consists of CELITE 209.

6. An insecticidal natural bait composition according to claim 1 wherein said diatomaceous silica consists of CELITE 322.

7. An insecticidal natural bait composition according to claim 1 wherein said sugar is invert sugar.

8. An insecticidal natural bait composition according to claim 1 wherein said sugar is sucrose.

9. An insecticidal natural bait composition according to claim 1 wherein said sugar is a mixture of sucrose and honey.

10. An insecticidal natural bait composition according to claim 1 wherein said sugar is glucose.

11. An insecticidal natural bait composition according to claim 1 wherein said sugar is a mixture of glucose and honey.

12. An insecticidal natural bait composition according to claim 1 wherein said sugar is dextrose.

13. An insecticidal natural bait composition according to claim 1 wherein said sugar is a mixture of dextrose and honey.

14. An insecticidal method which comprises contacting insects with a composition as defined in claim 1.

* * * * *